United States Patent [19]

Nishihira et al.

[11] Patent Number: 5,380,906
[45] Date of Patent: Jan. 10, 1995

[54] PROCESS FOR PREPARING CARBONIC DIESTER

[75] Inventors: Keigo Nishihira; Shuji Tanaka; Kunioki Kodama; Takayoshi Kaneko; Tetsuro Kawashita; Yuki Nishida; Tokuo Matsuzaki; Koji Abe, all of Ube, Japan

[73] Assignee: UBE Industries, Ltd., Yamaguchi, Japan

[21] Appl. No.: 25,384

[22] Filed: Mar. 2, 1993

Related U.S. Application Data

[63] Continuation-in-part of Ser. No. 841,009, Feb. 25, 1992, abandoned.

[30] Foreign Application Priority Data

| Mar. 1, 1991 | [JP] | Japan | 3-57695 |
| Jan. 24, 1992 | [JP] | Japan | 4-10867 |
| Mar. 6, 1992 | [JP] | Japan | 4-097506 |
| Jun. 30, 1992 | [JP] | Japan | 4-210601 |
| Jul. 31, 1992 | [JP] | Japan | 4-245411 |

[51] Int. Cl.$^6$ .............................. C07C 69/96
[52] U.S. Cl. ............................ 558/210; 558/377
[58] Field of Search .................. 558/260, 277

[56] References Cited

U.S. PATENT DOCUMENTS

4,384,133  5/1983  Miyazaki et al. ............ 560/204
5,162,563 11/1992  Nishihira et al. ............ 558/260

FOREIGN PATENT DOCUMENTS

425197  5/1991  European Pat. Off. .

OTHER PUBLICATIONS

Derwent Publication No. 85-267457, Database WPIL, corresponding to Japanese Patent Application No. 60-181051 (Toa Nenryo Kogio KK), 1985.
European Search Report, EP 92 10 3454, dated Dec. 18, 1992.

*Primary Examiner*—José G. Dees
*Assistant Examiner*—Dwayne C. Jones
*Attorney, Agent, or Firm*—Finnegan, Henderson, Farabow, Garrett & Dunner

[57] ABSTRACT

Disclosed is a process for preparing carbonic diester comprising the formation of carbonic diester by the vapor phase catalytic reaction of an alkyl nitrite and carbon monoxide in the presence of a solid catalyst, wherein platinum group metal ion in the solid catalyst is exchanged on an ion exchange zeolite carrier.

19 Claims, No Drawings

PROCESS FOR PREPARING CARBONIC DIESTER

This application is continuation-in-part of U.S. patent application Ser. No. 07/841,009, filed Feb. 25, 1992 now abandoned in the names of Keigo NISHIHIRA, Shuji TANAKA, Kunioki KODAMA, and Takayoshi KANEKO.

BACKGROUND OF THE INVENTION

The present invention relates to a process for preparing a carbonic dialkyl ester or dialkyl carbonate (to be referred to as carbonic diester) such as dimethyl carbonate by reaction of an alkyl nitrite such as methyl nitrite and carbon monoxide by vapor phase catalytic in the presence of a solid catalyst, wherein platinum group metal ion is exchanged on an ion exchange zeolite carrier.

Carbonic dialkylesters such as dimethyl carbonate are extremely useful as raw materials and for synthesis of aromatic polycarbonates and various chemical products, and as solvents.

For example, a process is proposed in Japanese Unexamined Patent Publication No. 181051/1985 for the preparation of dimethyl carbonate by reacting methyl nitrite and carbon monoxide in the vapor phase in the presence of a solid catalyst, wherein a platinum group metal or its compound is carried on a carrier such as activated carbon, and oxidant at 10 mol % or more as oxygen per carbon monoxide.

However, in this process, despite an oxidant such as oxygen being present in the above-mentioned proportion with respect to carbon monoxide in order to suppress production of dimethyl oxalate byproduct, a considerable amount of dimethyl oxalate is produced at high selectivity. This results in the problems of decreased selectivity of dimethyl carbonate, reduced reaction rate and low space time yield (STY to be described later). In addition, when reacting the mixed gas consisting of methyl nitrite, carbon monoxide, oxygen and so forth, there is the risk of explosion thus resulting in additional problems in terms of safety during the reaction.

More recently, a process for preparing dimethyl carbonate by vapor phase Catalytic reaction of carbon monoxide and methyl nitrite is disclosed in Japanese Unexamined Patent Publication No. 141243/1991 (Japanese Patent Application No. 274816/1989. In this process, a solid catalyst is used wherein a halogen compound such as a chloride of a platinum group metal, and a halogen compound such as the chloride of a secondary component metal selected from the group consisting of iron, copper, cobalt, nickel and tin, are carried on activated carbon and so on.

Moreover, Japanese Unexamined Patent Publication No. 89458/1992 (Japanese Patent Application No. 201146/1990) discloses a modified process wherein a minute amount of hydrogen chloride is added to the reaction system in the above-mentioned preparing of dimethyl carbonate.

However, in the above-mentioned preparing processes, the activity of the catalyst gradually decreases due to the releasing (dispersing) of minute amounts of chlorine from the catalyst. Thus, in order to prevent this, it is necessary to supply a minute amount of hydrogen chloride to the reaction system. As a result, said processes have the problems of chlorine ending up contaminating the target product of dimethyl carbonate, and the potential for the reaction apparatus being corroded by the chlorine.

SUMMARY OF THE INVENTION

The object of the present invention is to provide a process for the preparing of carbonic diester wherein there is no occurrence of problems caused by the presence of chlorine as in the above-mentioned prior art during preparing of carbonic diester from alkyl nitrite and carbon monoxide in the vapor phase in the presence of a solid catalyst, catalyst activity can be maintained at a high level for a long period of time, and dimethyl carbonate can be manufactured at high selectivity (and-/or high yield) under mild reaction conditions.

The inventors of the present invention discovered that the problems caused by the presence of chlorine in the above-mentioned prior art can be solved by the formation of carbonic diester by reacting alkyl nitrite with carbon monoxide using a solid catalyst that is obtained by ion exchange of a platinum group metal ion such as palladium on an ion exchange zeolite carrier, thus leading to completion of the present invention.

In other words, the present invention relates to a process for preparing carbonic diester comprising the formation of carbonic diester by the vapor phase catalytic reaction of an alkyl nitrite and carbon monoxide in the presence of a solid catalyst, wherein platinum group metal ion in the solid catalyst is exchanged on an ion exchange zeolite carrier.

DESCRIPTION OF THE PREFERRED EMBODIMENTS

In the present invention, a process for preparing dialkyl carbonate by vapor phase catalytic reaction of alkyl nitrite and carbon monoxide in the presence of a solid catalyst having weak acidity, wherein palladium ion is exchanged on an ion exchange zeolite carrier, using a raw material gas wherein the mole ratio of alkyl nitrite and carbon monoxide (RONO/CO) is 2–30 (and particularly 2–20), is particularly preferable (R: alkyl group).

In the preparing process of the present invention, the mole ratio of alkyl nitrite and carbon monoxide (RONO/CO) in the raw material gas used in the vapor phase catalytic reaction is 2 or more, preferably 2–30, more preferably 2–20, and even more preferably 3–10.

In the present invention, the vapor phase catalytic reaction of alkyl nitrite and carbon monoxide at a mole ratio (RONO/CO) of 2 or more in the presence of a solid catalyst, wherein a platinum group metal ion is exchanged on an ion exchange zeolite carrier, is most characteristic. When the mole ratio of alkyl nitrite and carbon monoxide (RONO/CO) is smaller than 2, the selectivity of the carbonic diester in the above-mentioned vapor phase catalytic reaction does not often become adequate.

In the present invention, the alkyl nitrite and carbon monoxide are preferably supplied to the reaction system either separately or in the form of a mixed gas after diluting with an inert gas such as nitrogen gas. It is also preferable from the viewpoint of safety that the concentration of alkyl nitrite be 30% by volume or less with respect to all of the feed gases (total volume) that are fed in the form of the raw material gas. In addition, it is preferable in terms of productivity on an industrial scale that the concentration of carbon monoxide be 1% by volume or more with respect to all of the feed gases (total volume).

The above-mentioned alkyl nitrite can be obtained in the form of a gas containing alkyl nitrite by reacting nitrogen monoxide, an oxygen-containing gas (for example, air) and a lower alcohol, and the reaction gas can be used directly in the present invention.

As a nitrite to be used in the present invention, there may be suitably mentioned a nitrite of a lower aliphatic monohydric alcohol having 1 to 5 carbon atoms such as methyl nitrite, ethyl nitrite, n- (or iso-) propyl nitrite and n- (or iso- or sec-) butyl nitrite; a nitrite of an alicyclic alcohol such as cyclohexyl nitrite; a nitrite of an aralkyl alcohol such as benzyl nitrite and phenylethyl nitrite; and the like, but particularly preferably a nitrite of a lower aliphatic monohydric alcohol having 1 to 5 carbon atoms, and above all, methyl nitrite and ethyl nitrite are most preferred. Such a nitrite can be easily obtained by oxidizing with oxygen part of $NO_x$ gas obtained by the reaction of sodium nitrite and an acid such as nitric acid, hydrochloric acid and sulfuric acid, or obtained by air oxidation of ammonia, to obtain $NO_x$ gas comprising $NO/NO_2 = 1/1$ (volume ratio) and then contacting an alcohol thereto.

Further, in the process of the present invention, a nitrite generates, after participating the reaction, nitrogen monoxide by decomposition thereof. Thus, it is preferred that the nitrogen monoxide is recovered from a reaction gas led out from a reactor, reacted with oxygen and an alcohol corresponding to a nitrite to be used to convert it to a nitrite again and used by circulation.

In the above-mentioned vapor phase catalytic reaction using a solid catalyst of the present invention, the vapor phase catalytic reaction of alkyl nitrite and carbon monoxide in the presence of water at a ratio of 0.01–5 mol % (vol %), and particularly 0.1–3 mol % (vol %), with respect to the total amount (total volume) of raw material gas supplied to the reaction system, is particularly preferable since it allows the activity of the solid catalyst to be maintained at a high level for a long period of time.

In addition, in the above-mentioned vapor phase catalytic reaction of the present invention, the vapor phase catalytic reaction of alkyl nitrite and carbon monoxide in the presence of water at a ratio of 0.01–5 mol % (vol %), and a lower aliphatic alcohol at a ratio of 0.03–30 mol % (vol %), particularly 0.05–20 mol % (vol %), and more particularly 0.1–15 mol % (vol %), with respect to the total amount (total volume) of raw material gas supplied to the reaction system, is preferable.

Examples of the above-mentioned lower aliphatic alcohol include methanol, ethanol, propanol and isopropanol. In addition, in the present invention, the space velocity of all raw material gases (total volume) containing carbon monoxide and alkyl nitrite that are supplied to a reactor filled with solid catalyst is preferably within a range of 500–20000 $h^{-1}$, and particularly preferably within a range of 2000–100000 $h^{-1}$.

In the preparing process of the present invention, the vapor phase catalytic reaction of carbon monoxide and alkyl nitrite can be carried out under extremely mild conditions. For example, it is preferable for said reaction to be carried out at a reaction temperature of 0°–200° C., and particularly 50°–150° C., and a reaction pressure of atmospheric pressure or under pressurization (particularly at a pressure of roughly 1–20 $kg/cm^2G$).

In the present invention, although the vapor phase catalytic reaction can be carried out in the vapor phase using a batch type or continuous process, a continuous process is industrially advantageous. The form in which the solid catalyst is present in the reaction system is such that the reaction can be carried using either a fixed bed, moving bed or fluid bed for the reactor.

In the present invention, a reaction gas is produced from the reaction system, wherein carbonic diester is formed by the above-mentioned vapor phase catalytic reaction, containing by-products such as oxalic diesters, unreacted carbon monoxide, alkyl nitrites such as methyl nitrite, nitrogen monoxide, carbon dioxide and inert gases in addition to the target product carbonic diester such as dimethyl carbonate. For example, by cooling the reaction gas wherein dimethyl carbonate has formed in the manner described above, in addition to the target product of dialkyl carbonate, by-products such as dimethyl oxalate are condensed and separated in the form of a reaction liquid. On the other hand, it is preferable that uncondensed gases such as carbon monoxide, methyl nitrite, nitrogen monoxide, carbon dioxide and inert gases are circulated to the reaction system while a portion of those gases are purged.

On the other hand, the reaction liquid (condensed liquid) obtained in the manner described above can be separated and purified by, for example, separating and purifying the carbonic diester such as dimethyl carbonate (the target product) by conventional methods such as distillation.

In addition, the above-mentioned uncondensed gases that are again circulated to the reactor should be added to the raw material gas, should be prepared to a specific amount and should be circulated to the contact catalytic reaction system. Water and/or a lower aliphatic alcohol may be contained in the circulated gas, if necessary.

The solid catalyst used in the preparing process of the present invention is preferably a solid catalyst having weak acidity, wherein a platinum group metal ion, such as palladium, platinum, iridium, ruthenium or rhodium ion, is exchanged on an ion exchange zeolite carrier, and is particularly preferably a solid catalyst having weak acidity wherein at least palladium ion is exchanged on an ion exchange zeolite carrier.

In the above-mentioned solid catalyst, the amount of platinum group metal ion (particularly palladium ion) exchanged on an ion exchange zeolite carrier is the amount wherein the ratio of platinum group metal ion (as platinum group metal ion) to zeolite carrier is preferably 0.1–10% by weight, particularly preferably 0.1–8% by weight, and more particularly preferably 0.5–5% by weight.

The above-mentioned solid catalyst may be a solid catalyst wherein, in addition to platinum group metal ion, metal ion of metals of groups 1b–7b and metals of group 8 (excluding platinum group metals, alkaline metals and alkaline earth metals) of the periodic table, such as copper, iron, tin, nickel, cobalt, silver, cerium or manganese, is exchanged on an ion exchange zeolite carrier so as not to increase the acid site on the carrier. In the present invention, since metal ions of metals of groups 1b–7b and group 8 of the periodic table generally increase the acid site on the carrier, a solid catalyst having weak acidity, wherein only a platinum group metal ion is exchanged on an ion exchange zeolite carrier, is preferable in terms of high space time yield and selectivity of the carbonic diester.

The zeolite carrier preferably used in preparation of the above-mentioned solid catalyst is either an ion exchange zeolite carrier wherein the ion exchange site of the zeolite (or a molecular sieve) is neutralized with alkaline metal ion or alkaline earth metal ion (a powdered zeolite carrier having a particle size of 20–100 μm, or granular zeolite carrier having a grain size of 4–200 mesh), or an ion exchange zeolite carrier wherein the above-mentioned zeolite carrier is further ion exchanged with hydrogen ion and ammonium ion (and particularly, a granular zeolite carrier having a grain size of roughly 5–100 mesh).

Furthermore, a powdered catalyst wherein platinum group metal ion is exchanged on an ion exchange zeolite carrier (powdered) can be used for the above-mentioned solid catalyst. Alternatively, it is preferable that said solid catalyst be used following mixing of a suitable binder into the powdered solid catalyst and molding into granules having a mean grain size of approximately 5–100 mesh.

The "zeolite having an ion exchange site" that serves as the ion exchange zeolite carrier used in preparation of the above-mentioned solid catalyst may be either be a synthetic zeolite, such as X zeolite, Y zeolite, Mordenite or silicalite, or a naturally occurring zeolite. The Si to Al atomic ratio of said zeolite is preferably roughly 0.5–10, particularly preferably 1–6, and more particularly preferably 2–5.

In the preparing process of the present invention, the use of a solid catalyst having weak acidity, wherein only palladium ion is exchanged on an "ion exchange zeolite carrier comprising Faujasite zeolite such as X zeolite or Y zeolite", in which the range of the atomic ratio of Si and Al is within roughly 1–10 (preferably 1–6 and more preferably 2–5), is particularly preferable.

A known support method, wherein a platinum group metal compound is added to an aqueous slurry of ion exchange zeolite carrier followed by ion exchange of metal ion on said zeolite carrier, can be used for the method for preparing the above-mentioned solid catalyst. A method of preparing a solid catalyst that can be used industrially is preferable by, for example, adding a complex of a platinum group metal halide, such as tetraamine palladium chloride, to an aqueous slurry in which an ion exchange zeolite carrier comprising X zeolite and Y zeolite is dispersed in water, performing ion exchange at a temperature of 5°–100° C., and particularly 30°–80° C., drying the product in a drying process, and molding with an extruder, tablet machine or granulator if necessary.

Although the above-mentioned drying process does not require any special procedure, drying over a temperature range from room temperature (approximately 20° C.) to 100°–120° C. while slowly raising the temperature over the course of 1–2 hours, and performing drying at that temperature for 1–24 hours, and particularly 2–10 hours, is preferable to form the uniformity of the catalyst.

In addition, in the above-mentioned molding of the solid catalyst, the mixing of a suitable binder into the above-mentioned dried product is preferable in order to improve moldability.

Moreover, in the preparation of the solid catalyst, after exchanging platinum group metal ion on a zeolite carrier and drying, the molded solid catalyst may be baked while flowing in air or an inert gas at a temperature that does not affect the crystal structure or composition of the zeolite carrier (for example, a range of approximately 150°–500° C. and preferably a temperature range of 200°–350° C.) for 1–10 hours.

Examples of the above-mentioned platinum group metal compounds that can be used preferably in the present invention include halides of platinum group metals, inorganic platinum group metallic salts such as nitrates and sulfates, organic platinum group metallic salts such as acetates and oxalates, or various types of complexes such as tetra-anmine complexes and ethylene diamine complexes of platinum group metal compounds in order to increase solubility in water and so on.

Specific examples of the above-mentioned platinum group metal compounds include palladium compounds such as palladium chlorides (particularly palladium dichloride), palladium acetate and palladium nitrate, the tetra-anmine complexes of those palladium compounds (particularly palladium chlorides), platinum chlorides, tetra-anmine platinum chlorides (complexes), iridium chloride, ruthenium chloride and rhodium chloride.

Moreover, it is particularly preferable that the solid catalyst used in the present invention be a solid catalyst having weak acidity, wherein together with the ion exchange site of an ion exchange zeolite carrier being ion exchange with platinum group metal ion, a portion (at least 10–90% and particularly 20–80%) of the ion exchange site (acid site) on said zeolite carrier other than the location at which platinum group metal ion is supported, is neutralized (or ion exchanged) with alkaline metal ion such as sodium or potassium, or alkaline earth metal ion such as magnesium or calcium.

In the case of the "solid catalyst having weak acidity, wherein platinum group metal ion and alkaline metal ion and/or alkaline earth metal ion are exchanged on the above-mentioned zeolite carrier", since the ion exchange site of the zeolite carrier (referring to an ion exchange site on the above-mentioned zeolite carrier other than that at which platinum group metal ion is exchanged on said zeolite carrier, and is the location of the acid site) is neutralized or exchanged with alkaline metal ion or alkaline earth metal ion, the acid site on the zeolite carrier is reduced considerably, resulting in a decrease in acid strength and acid amount of said resulting solid catalyst.

As a result, in the case of using the above-mentioned solid catalyst having weak acidity in a contact catalytic reaction of alkyl nitrite with carbon monoxide, said solid catalyst offers the advantage of allowing the side reaction rate to be held to a low level.

The acidity of a solid catalyst as in the above-mentioned solid catalyst is expressed according to the acid strength and acid amount. In general, acid strength is determined by a temperature programmed desorption method (TPD method), and is expressed as a relative value to acid amount by a TPD method.

In the present invention, it is desirable to use a solid catalyst demonstrating weak acid strength having a "desorption temperature of less than 360° C." as indicated with the desorption temperature determined by the ammonia-temperature programmed desorption method (ammonia-TPD method) prescribed by the Catalyst Society.

In particular, it is preferable that the solid catalyst used in the present invention have weak acid strength such that the peak desorption temperature according to the above-mentioned ammonia-TPD method (desorption temperature, an indicator of acid strength) is 350° C. or lower (particularly approximately 330° C. or lower), and does not essentially demonstrate a peak desorption temperature at approximately 360° C. or higher (particularly 350° C. or lower). High acidity solid catalysts, which have an acid site that demonstrates excessively strong acid strength, are not preferable since these cause undesirable side reactions in the above-mentioned vapor phase catalytic reaction.

In addition, it is preferable that the "acid amount (total area of each desorption peak by the TPD method)" that relates to the amount of the acid site of the solid catalyst as measured by, for example, the ammonia-TPD method, be 20 or less, particularly 1–10, and preferably 1–6 in the case of taking the "acid amount" relating to the amount of the acid site of HY zeolite measured according to the above-mentioned ammonia-TPD method, to be 100.

Preparation of the above-mentioned "solid catalyst, wherein platinum group metal ion and alkaline metal ion and/or alkaline earth metal ion are exchanged on the above-mentioned zeolite carrier" is preferably performed using a method wherein, for example, after adding alkaline metal compound or alkaline earth metal compound to an aqueous slurry of the above-mentioned ion exchange zeolite carrier and neutralizing the acid site of the above-mentioned zeolite carrier with alkaline metal ion and/or alkaline earth metal ion, platinum group metal compound is added to the aqueous slurry of neutralized zeolite carrier, platinum group metal ion is exchanged on the zeolite carrier and said zeolite carrier is dried followed by molding and baking as necessary.

At the time of the "neutralization procedure" in the above-mentioned preparation of the solid catalyst, the alkaline metal compound or alkaline earth metal compound may be added as is to the aqueous slurry solution of the zeolite, or an aqueous solution of alkaline metal compound or an aqueous solution of alkaline earth metal compound may be added to the above-mentioned aqueous slurry of the zeolite.

Examples of the above-mentioned alkaline metal compound include salts of organic acids such as sodium acetate, potassium acetate and sodium oxalate, and salts of inorganic acids such as $NaNO_3$, $Na_2SO_4$, NaCl and KCl.

Examples of the above-mentioned alkaline earth metal compound include salts of inorganic acids such as cerium chloride, calcium chloride, magnesium chloride, barium chloride, calcium nitrate, barium nitrate, magnesium nitrate and magnesium phosphate, and salts of organic acids such as calcium acetate and barium acetate.

Although the following provides a detailed explanation of the process of the present invention through its examples and comparative examples, the process of the present invention is not limited to said examples and comparative examples whatsoever.

Furthermore, the space time yield (STY) (g/l.h) in each of the examples and comparative examples was determined from the following equation using "$\theta$" (hr) to represent the contact catalytic reaction time of carbon monoxide and methyl nitrite, "a" (g) to represent the amount of dimethyl carbonate formed during that time, and "b" (l) to represent the amount of catalyst filled into the reaction tube.

$STY$ (Space Time Yield) $= a/(b \times \theta)$

In addition, the selectivities X and Y in each of the examples and comparative examples indicate the selectivity of dimethyl carbonate based on carbon monoxide and based on the methyl nitrite, respectively. Said selectivities X and Y were determined from the following equations using "c" (mol), "d" (mol), "e" (mol), "f" (mol) and "g" (mol) to represent the amounts of dimethyl carbonate, dimethyl oxalate, carbon dioxide, methyl formate and methylal formed during the above-mentioned time $\theta$ (hr), respectively.

$X$ (Selectivity) $= \{c/(c+2xd+e)\} \times 100$ $Y$ (Selectivity) $= \{c/(c+d+2xf+g)\} \times 100$

EXAMPLE 1

1) Preparation of Solid Catalyst 10 g of NaY zeolite carrier (having an atomic ratio (Si/Al) of 2.5) were added to 200 ml of distilled water to prepare the zeolite carrier aqueous slurry. Next, 50 ml of an aqueous solution, in which 0.24 g of tetra-anmine palladium chloride (Pd: 1 millimole) is dissolved, were dropped into the above-mentioned aqueous slurry over the course of 30 minutes while stirring and heating said aqueous slurry to 70° C. After stirring while maintaining the temperature at 70° C. for 3 hours and ion exchanging the palladium ion on the above-mentioned zeolite carrier, the resulting aqueous slurry was cooled to room temperature followed by filtration and washing with water to obtain a cake-like catalyst.

After placing this wet cake-like catalyst in a drier and drying for 5 hours at 100° C. the dried catalyst was heat treated (drying and baking) for 2 hours at 200° C. in the presence of flowing air resulting in the preparing of a solid catalyst wherein palladium ion is exchanged and carried (or loaded) on a Y zeolite carrier.

After molding this solid catalyst with a tablet molding machine and grinding, the resulting particles were passed through a sieve to give the particles a uniform size of 10 mesh to form granules of the solid catalyst.

When the amount of carried palladium ion of the solid catalyst prepared in the manner described above was analyzed using an atomic absorption spectrometer after dissolving with aqua regia, the amount of carried palladium ion was 0.95% by weight, and the amount of carried sodium ion was 8.86% by weight.

In addition, when the acid strength of the above-mentioned solid catalyst was measured according to the ammonia-TPD method, desorption peaks were observed at roughly 195° C. and 305° C., and there were essentially no other peaks present at temperatures higher than the above. In addition, the acid amount of the solid catalyst (according to the ammonia-TPD method) was 10% or less of the acid amount of HY zeolite.

2) Preparation of Dimethyl Carbonate 5 ml of the above-mentioned solid catalyst were filled into a reaction tube having an outer diameter of 20 mm (with external jacket), the reaction tube was fixed in a vertical position, heating medium was circulated through the reaction tube jacket, and heating was controlled so that the temperature inside the solid catalyst layer was 120° C.

Raw material gas (having a water content of 0.3 mol % with respect to the entire raw material gas), comprising a composition ratio of 15% by volume of methyl nitrite, 5% by volume of carbon monoxide, 3% by volume of nitrogen monoxide, 2% by volume of methanol and 75% by volume of nitrogen, was fed from the top of the reaction tube at a space velocity (GHSV) of 4000 $h^{-1}$. A vapor phase catalytic reaction was then carried out between methyl nitrite and carbon monoxide for 50 hours under atmospheric pressure while maintaining the reaction temperature at 120° C.

In the above-mentioned vapor phase catalytic reaction, as a result of capturing the reaction gas discharged from the reaction tube from the start of the reaction until 8 hours after the start of the reaction by passing through ice-cooled methanol, and analyzing the captured liquid by gas chromatography, it was confirmed that dimethyl carbonate was formed at an initial space time yield (initial STY) of 390 g/l.h, the initial selectivity of dimethyl carbonate based on carbon monoxide was 85%, and the initial selectivity of dimethyl carbonate based on methyl nitrite was 81%. In addition, the presence of byproducts, in the form of dimethyl oxalate, carbon dioxide, methyl formate and methylal, was also confirmed.

Moreover, the space time yield (STY) and selectivities for the dimethyl carbonate formed in the reaction gas when the above-mentioned vapor phase catalytic reaction was continued for 50 hours remained, essentially unchanged in comparison with the initial space time yield (initial STY) and initial selectivities of dimethyl carbonate (percentage of DMC-STY dropping: within 5%).

EXAMPLES 2–4

With the exception of changing the compositions of methyl nitrite, carbon monoxide and nitrogen gas in the raw material gas, vapor phase catalytic reactions were respectively carried out in the same manner as Example 1 using the solid catalyst prepared in Example 1. The results for "each of the initial space time yields (initial STY) and selectivities of dimethyl carbonate" in these vapor phase catalytic reactions are respectively indicated in Table 1.

Moreover, there were essentially no changes in each of the time space yields and selectivities for dimethyl carbonate when the above-mentioned vapor phase catalytic reactions were continued for 50 hours in these examples in comparison with each of the initial space time yields and selectivities.

EXAMPLE 5

1) Preparation of Solid Catalyst

With the exception of changing the amount of tetraanmine palladium chloride to 0.50 g, a solid catalyst, wherein palladium ion is exchanged on the above-mentioned zeolite carrier, was prepared in the same manner as Example 1.

The amount of carried palladium ion of the solid catalyst prepared in the manner described above was 2.07% by weight, while the amount of carried sodium ion was 8.43% by weight.

In addition, the acid strength of the above-mentioned solid catalyst as measured with the ammonia-TPD method demonstrated desorption peak temperatures of approximately 195° C. and 305° C., there were essentially no other desorption peaks at temperatures higher than the above. In addition, the acid amount of this solid catalyst was 10% or less of the acid amount of HY zeolite.

2) Preparation of Dimethyl Carbonate

With the exception of using 5 ml of the above-mentioned solid catalyst, a vapor phase catalytic reaction was carried out in the same manner as Example 1. The results for "each of the initial space time yields (initial STY) and selectivities of dimethyl carbonate" in this vapor phase catalytic reaction are respectively indicated in Table 1.

Moreover, there were essentially no changes in the space time yield and selectivities of dimethyl carbonate in comparison with the initial space time yield and selectivities when the above-mentioned vapor phase catalytic reaction was continued for 50 hours in this Example.

EXAMPLES 6–7

1) Preparation of Solid Catalysts

With the exception of using NaX zeolite (Si/Al=1.23: Example 6) or Na Mordenite (Si/Al=9.50: Example 7) in place of NaY zeolite, solid catalysts, wherein palladium ion is exchanged on a zeolite carrier, were respectively prepared in the same manner as Example 1.

Each of the amounts of carried palladium of the respective solid catalysts prepared as described above was 0.98% by weight (Example 6) or 0.92% by weight (Example 7). When the respective acid strengths were measured by the ammonia-TPD method, desorption peaks were observed at approximately 280° C. (Example 6) and approximately 340° C. (Example 7), respectively. Desorption peaks were essentially not presented at higher temperatures in either case. In addition, although the acid amount of the solid catalyst (according to the ammonia-TPD method) was 10% or less of the acid amount of HY zeolite in Example 6, it was roughly 15% of the acid amount of HY zeolite in Example 7.

2) Preparation of Dimethyl Carbonate

With the exception of using each of the above-mentioned solid catalysts, vapor phase catalytic reactions were carried out in the same manner as Example 1 in Examples 6 and 7. The results of those vapor phase catalytic reactions are respectively indicated in Table 1.

Moreover, the space time yields and selectivities of dimethyl carbonate formed in the reaction gas when each of the above-mentioned vapor phase catalytic reactions were continued for 50 hours in these examples remained essentially unchanged in comparison with the initial space time yield and initial selectivities for dimethyl carbonate, respectively.

EXAMPLE 8

1) Preparation of Solid Catalyst

With the exception of drying the wet cake-like catalyst for 5 hours at 100° C. and heat treating (drying and baking) for 3 hours at 300° C. in the presence of flowing air, the granular form of a solid catalyst (grain size: 10 mesh), wherein palladium ion is exchanged on a Na—Y zeolite carrier, was manufactured in the same manner as Example 1.

When the amount of carried palladium ion of the solid catalyst prepared in the manner described above was analyzed with an atomic absorption spectrometer after dissolving with aqua regia, the amount of carried palladium ion was 0.95% by weight, and the amount of carried sodium ion was 8.85% by weight.

In addition, when the acid strength of the above-mentioned solid catalyst was measured with the ammonia-TPD method, desorption peaks were observed at approximately 195° C. and 305° C., and there were essentially no desorption peaks present at higher temperatures. In addition, the acid amount (according to the ammonia-TPD method) of the solid catalyst was 10% or less of the acid amount of HY zeolite.

2) Preparation of Dimethyl Carbonate

With the exception of using 2.5 ml of the above-mentioned solid catalyst, using a raw material gas (having a water content of 0.3 mol % with respect to the total amount of raw material gas) composed of 18% by volume of methyl nitrite, 2% by volume of carbon monoxide, 3% by volume of nitrogen monoxide, 2% by volume of methyl alcohol and 75% by volume of nitrogen, supplying said raw material gas to the reaction system at a space velocity of 8000 $h^{-1}$, and controlling heating so that the reaction temperature was 110° C., a vapor phase catalytic reaction was carried out in the same manner as Example 1.

The results for "each of the initial space time yields (initial STY) and selectivities for dimethyl carbonate" in this vapor phase catalytic reaction are indicated in Table 2.

There were essentially no changes in the time space yield and selectivities for dimethyl carbonate in comparison with the initial time space yield and selectivities when the above-mentioned vapor phase catalytic reaction was continued for 50 hours in this example (percentage of DMC-STY dropping: within 5%).

EXAMPLES 9-11

With the exception of using the solid catalyst prepared in Example 8 and changing water content of the raw material gas as indicated in Table 2, vapor phase catalytic reactions were respectively carried out in the same manner as Example 8. The results for those vapor phase catalytic reactions are respectively indicated in Table 2.

There were essentially no changes in the space time yields and selectivities with respect to dimethyl carbonate in comparison with the initial space time yields and initial selectivities of dimethyl carbonate when the above-mentioned vapor phase catalytic reactions were respectively continued for 50 minutes in Examples 9 and 10 (percentage of DMC-STY dropping: within 5%).

In addition, in Example 11, the space time yield with respect to dimethyl carbonate formed in the reaction gas when the above-mentioned vapor phase catalytic reactions were respectively continued for 10 hours decreased to 330 g/l.h (percentage of DMC-STY dropping: 13.1%).

EXAMPLE 12

With the exception of using the solid catalyst prepared in Example 8 and setting the reaction pressure to 3 kg/cm$^2$G, a vapor phase catalytic reaction was carried out in the same manner as Example 8. The results for that vapor phase catalytic reaction are indicated in Table 2.

EXAMPLE 13

With the exception of using 2.5 ml of the solid catalyst prepared in Example 8, using a raw material gas (having a water content of 0.4 mol % with respect to the entire raw material gas) composed of 18% by volume of methyl nitrite, 3% by volume of carbon monoxide, 3% by volume of nitrogen monoxide, 2% by volume of methanol and 74% by volume of nitrogen, supplying said raw material gas to the reaction system at a space velocity of 8000 $h^{-1}$, controlling heating so that the reaction temperature was 105° C., and setting the reaction pressure to 3 kg/cm$^2$G, a vapor phase catalytic reaction was carried out in the same manner as Example 8.

The results for "each of the initial space time yields (initial STY) and selectivities of dimethyl carbonate" in this vapor phase catalytic reaction are indicated in Table 2.

There were essentially no changes in the time space yield and selectivities for dimethyl carbonate that formed when the above-mentioned vapor phase catalytic reaction was continued for 50 hours in this example in comparison with the initial time space yield and initial selectivities for dimethyl carbonate (percentage of DMC-STY dropping: within 5%).

EXAMPLES 14-16

With the exception of the changing the composition of the raw material gas as indicated in Table 2, vapor phase catalytic reactions were respectively carried out in the same manner as Example 13. The results for those vapor phase catalytic reactions are respectively indicated in Table 2.

EXAMPLE 17

With the exception of changing the reaction pressure to atmospheric pressure, a vapor phase catalytic reaction was carried out in the same manner as Example 13. The results for that vapor phase catalytic reaction are indicated in Table 2.

EXAMPLE 18

1) Preparation of Solid Catalyst 10.1 g of NaY zeolite having an atomic ratio (Si/Al) of 2.75 (Tosoh: HSZ-320NAA) were weighed into a 500 ml beaker followed by the addition of 300 ml of distilled water to prepare an aqueous zeolite slurry. This aqueous slurry was then boiled for 1 hour while stirring with a magnetic stirrer.

300 ml of 1N NaNO$_3$ were added to the zeolite obtained after filtering this aqueous slurry followed by stirring for 20 hours at room temperature. After filtering this solution and washing with 200 ml of distilled water, an additional 250 ml of distilled water were added to prepare an aqueous zeolite slurry. A solution containing 0.25 g of tetra-anmine palladium chloride dissolved in 50 ml of distilled water was dropped into this slurry while stirring gently over the course of 30 minutes. Moreover, after completion of this dropping and allowing the solution to stand for 1 day while stirring to exchange palladium ion on the zeolite carrier, the aqueous slurry was filtered and washed three times with 200 ml of distilled water.

The resulting aqueous slurry was cooled to room temperature, filtered and washed to obtain a cake-like catalyst. After placing this wet cake-like catalyst in a drier and drying first for 2 hours at 70° C. and then 5 hours at 120° C., molding this with a tablet molding machine and grinding, the resulting particles were passed through a sieve to give the particles a uniform size of 10 mesh to form granules of the solid catalyst.

The above-mentioned granules of the solid catalyst were filled into a glass tube equipped with a perforated plate, and heated by raising the temperature from room temperature to 300° C. over the course of roughly 1.5 hours while flowing in air at a flow rate of 30 liters/h to bake for 3 hours at that final temperature.

When the amount of carried palladium ion of the solid catalyst prepared in the manner described above was analyzed using an atomic absorption spectrophotometer after dissolving with aqua regia, the amount of carried palladium ion was 0.95% by weight, and the amount of carried sodium ion was 8.85% by weight.

In addition, when the acid strength of the above-mentioned solid catalyst was measured according to the ammonia-TPD method, desorption peaks were observed at approximately 195° C. and 305° C., and there were essentially no other peaks present at temperatures higher than the above. In addition, the acid amount of the solid catalyst (according to the ammonia-TPD method) was 10% or less of the acid amount of HY zeolite.

2) Preparation of Dimethyl Carbonate

After filling 2.5 ml of the above-mentioned solid catalyst into a stainless steel vapor phase reactor having an inner diameter of 10 mm (with external jacket), the reaction tube was fixed in a vertical position, heating medium was circulated through the reaction tube jacket, and heating was controlled so that the temperature inside the solid catalyst layer was 110° C.

A mixed gas of carbon monoxide and a gas containing nitrogen monoxide, oxygen and methyl nitrite synthesized from methanol with nitrogen monoxide (a mixed gas comprising a composition of 15% by volume of methyl nitrite, 5% by volume of carbon monoxide, 3% by volume of nitrogen monoxide, 2% by volume of methanol and 75% by volume of nitrogen (having a water content of 0.05% by volume with respect to the entire raw material gas)), was fed from the top of the reaction tube at a space velocity (GHSV) of 8000 $h^{-1}$. A vapor phase catalytic reaction was then carried out between methyl nitrite and carbon monoxide for 500 hours while maintaining the reaction temperature at 110° C. and regulating the pressure of 3 $kg/cm^2G$ at a valve provided at the outlet of the reactor.

In the above-mentioned vapor phase catalytic reaction, as a result of capturing the reaction gas discharged from the reaction tube from the start of the reaction until 8 hours after the start of the reaction by passing through ice-cooled methanol, and analyzing the captured liquid by gas chromatography, it was confirmed that dimethyl carbonate was formed at an initial space time yield (initial STY) of 380 g/l.h, the selectivity of dimethyl carbonate based on carbon monoxide was 88%, and the selectivity of dimethyl carbonate based on methyl nitrite was 81%.

The space time yield and selectivities of the dimethyl carbonate after 70 hours in the above-mentioned vapor phase catalytic reaction remained essentially unchanged in comparison with the initial space time yield (initial STY) and initial selectivities of dimethyl carbonate (percentage of DMC-STY dropping: within 5%).

Moreover, the space time yield of dimethyl carbonate after 500 hours in the above-mentioned vapor phase catalytic reaction was 345 g/l.h (percentage of DMC-STY dropping: 10%).

EXAMPLE 19

1) Preparation of Solid Catalyst

With the exception of using NaY zeolite having an atomic ratio (Si/Al) of 2.5 (Shokubai Kasei Kogyo Ltd.: ZCE-50), a solid catalyst was prepared, wherein palladium ion is exchanged on a zeolite carrier, in the same manner as Example 18. The solid catalyst prepared in the manner described above had the amount of carried metal ion and properties indicated in Table 3, and the acid amount was nearly the same as the solid catalyst of Example 18.

2) Preparation of Dimethyl Carbonate

With the exception of using the above-mentioned solid catalyst, a vapor phase catalytic reaction was carried out in the same manner as Example 18. The results of that vapor phase catalytic reaction are indicated in Table 3.

EXAMPLE 20

1) Preparation of Solid Catalyst

With the exception of using NaX zeolite having an atomic ratio (Si/Al) of 1.23 (Union Showa Ltd.: Molecular Sieve 13X), a solid catalyst, wherein palladium ion was exchanged on the above-mentioned zeolite carrier, was prepared in the same manner as Example 18.

The solid catalyst prepared in the manner described above had the amount of carried metal ion and properties indicated in Table 3, and the acid amount was 1.5 times greater than the solid catalyst of Example 18.

2) Preparation of Dimethyl Carbonate

With the exception of using the above-mentioned solid catalyst, a vapor phase catalytic reaction was carried out in the same manner as Example 18. The results of that vapor phase catalytic reaction are indicated in Table 3.

EXAMPLE 21

1) Preparation of Solid Catalyst

With the exception of changing the amount of tetraanmine palladium chloride used to 0.50 g, a solid catalyst, wherein palladium ion was exchanged on the above-mentioned zeolite carrier, was prepared in the same manner as Example 18.

The solid catalyst prepared in the manner described above had the amount of carried metal ion and properties indicated in Table 3, and the acid amount was 1.8 times greater than the solid catalyst of Example 18.

2) Preparation of Dimethyl Carbonate

With the exception of using the above-mentioned solid catalyst, a vapor phase catalytic reaction was carried out in the same manner as Example 18. The results of that vapor phase catalytic reaction are indicated in Table 3.

EXAMPLE 22

1) Preparation of Solid Catalyst

With the exception of using 0.30 g of bis-ethylenediamine palladium chloride instead of 0.25 g of tetraanmine palladium chloride, a solid catalyst, wherein palladium ion was exchanged on a zeolite carrier, was prepared in the same manner as Example 18.

The solid catalyst prepared in the manner described above had the amount of carried metal ion and properties indicated in Table 3, and the acid amount was nearly the same as that of the solid catalyst of Example 18.

2) Preparing of Dimethyl Carbonate

With the exception of using the above-mentioned solid catalyst, a vapor phase catalytic reaction was carried out in the same manner as Example 18. The results of that vapor phase catalytic reaction are indicated in Table 3.

EXAMPLE 23

1) Preparation of Solid Catalyst

With the exception of using 300 ml of an aqueous solution of 0.3N CaCl₂ instead of 300 ml of an aqueous solution of 1N NaNO₃, filtering the aqueous slurry, adding the resulting zeolite and stirring for 2 days at room temperature, a solid catalyst, wherein palladium ion and calcium ion were exchanged on a zeolite carrier, was prepared in the same manner as Example 18.

The solid catalyst prepared in the manner described above had the amount of carried metal ion and properties indicated in Table 3, and the acid amount was 1.6 times greater than that of the solid catalyst of Example 18.

2) Preparation of Dimethyl Carbonate

With the exception of using the above-mentioned solid catalyst, a vapor phase catalytic reaction was carried out in the same manner as Example 18. The results of that vapor phase catalytic reaction are indicated in Table 3.

EXAMPLE 24

1) Preparation of Solid Catalyst

With the exception of using 300 ml of an aqueous solution of 0.3N LiOAc instead of 300 ml of an aqueous solution of 0.3N CaCl₂, a solid catalyst, wherein palladium and lithium ion are exchanged on a zeolite carrier, was prepared in the same manner as Example 23.

The solid catalyst prepared in the manner described above had the amount of carried metal ion and properties indicated in Table 3, and the acid amount was nearly the same as that of the solid catalyst of Example 18.

2) Preparation of Dimethyl Carbonate

With the exception of using the above-mentioned solid catalyst, a vapor phase catalytic reaction was carried out in the same manner as Example 18. The results of that vapor phase catalytic reaction are indicated in Table 3.

TABLE 1

| | | Characteristic of solid catalyst | | | | | | | | | |
|---|---|---|---|---|---|---|---|---|---|---|---|
| | Kind of zeolite carrier | Carried amount of metal ion (% by weight) | | | Acid strength: Elimination peak (°C.) | Acid amount: against HY type zeolite (%) | Condition of vapor phase catalytic reaction | | | | |
| | | | | | | | Composition of raw material gas (mol %) | | | | |
| | | $Pd^{++}$ | $Na^+$ | Other metals | | | $CH_3ONO$ (MN) | CO | NO | MeOH | $N_2$ | Water |
| Example 1 | Na-Y type zeolite | 0.95 | 8.86 | — | 195° C. 305° C. | 10 or less | 15 | 5 | 3 | 2 | 75 | 0.3 |
| Example 2 | Na-Y type zeolite | 0.95 | 8.86 | — | 195° C. 305° C. | 10 or less | 15 | 3 | 3 | 2 | 77 | 0.3 |
| Example 3 | Na-Y type zeolite | 0.95 | 8.86 | — | 195° C. 305° C. | 10 or less | 15 | 7 | 3 | 2 | 68 | 0.3 |
| Example 4 | Na-Y type zeolite | 0.95 | 8.86 | — | 195° C. 305° C. | 10 or less | 20 | 3 | 3 | 2 | 72 | 0.3 |
| Example 5 | Na-Y type zeolite | 2.07 | 8.43 | — | 195° C. 305° C. | 10 or less | 15 | 3 | 3 | 2 | 77 | 0.3 |
| Example 6 | Na-Y type zeolite | 0.98 | 14.3 | — | 280° C. | 10 or less | 15 | 5 | 3 | 2 | 75 | 0.3 |
| Example 7 | Na-Y type mordenite | 0.95 | 5.26 | — | 340° C. | about 15 | 15 | 3 | 3 | 2 | 77 | 0.3 |

| | Condition of vapor phase catalytic reaction | | | | Result of vapor phase contact reaction | | |
|---|---|---|---|---|---|---|---|
| | Space velocity of raw material gas ($h^{-1}$) | Reaction temperature (°C.) | Reaction pressure kg/cm² G | Reaction time (h) | STY of dimethyl carbonate (g/l-h) | Selectivity (%) | |
| | | | | | | Based on CO | Based on MN |
| Example 1 | 4000 | 120 | Atmospheric pressure | 0~8 50 | 390 (same level) | 85 — | 81 — |
| Example 2 | 4000 | 120 | Atmospheric pressure | 0~8 50 | 430 (same level) | 85 — | 80 — |
| Example 3 | 4000 | 120 | Atmospheric pressure | 0~8 50 | 310 (same level) | 80 — | 73 — |
| Example 4 | 4000 | 120 | Atmospheric pressure | 0~8 50 | 480 (same level) | 85 — | 81 — |
| Example 5 | 4000 | 120 | Atmospheric pressure | 0~8 50 | 460 (same level) | 85 — | 80 — |
| Example 6 | 4000 | 120 | Atmospheric pressure | 0~8 50 | 200 (same level) | 85 — | 80 — |
| Example 7 | 4000 | 120 | Atmospheric pressure | 0~8 50 | 120 (same | 76 | 73 |

TABLE 1-continued

|  |  |  | pressure | level) |
|---|---|---|---|---|

TABLE 2

| | Characteristic of solid catalyst | | | | | Condition of vapor phase catalytic reaction | | | | | |
|---|---|---|---|---|---|---|---|---|---|---|---|
| | Kind of zeolite carrier | Carried amount of metal ion (% by weight) | | | Acid strength: Elimination peak (°C.) | Acid amount: against HY type zeolite (%) | Composition of raw material gas (mol %) | | | | | |
| | | $Pd^{++}$ | $Na^+$ | Other metals | | | $CH_3ONO$ (MN) | CO | NO | MeOH | $N_2$ | Water |
| Example 8 | Na-Y type zeolite | 0.95 | 8.85 | — | 195° C. 305° C. | 10 or less | 18 | 2 | 3 | 2 | 75 | 0.3 |
| Example 9 | Na-Y type zeolite | 0.95 | 8.85 | — | 195° C. 305° C. | 10 or less | 18 | 2 | 3 | 2 | 75 | 0.5 |
| Example 10 | Na-Y type zeolite | 0.95 | 8.85 | — | 195° C. 305° C. | 10 or less | 18 | 2 | 3 | 2 | 74 | 0.8 |
| Example 11 | Na-Y type zeolite | 0.95 | 8.85 | — | 195° C. 305° C. | 10 or less | 18 | 2 | 3 | 2 | 74 | 1.5 |
| Example 12 | Na-Y type zeolite | 0.95 | 8.85 | — | 195° C. 305° C. | 10 or less | 18 | 2 | 3 | 2 | 75 | 0.3 |
| Example 13 | Na-Y type zeolite | 0.95 | 8.85 | — | 195° C. 305° C. | 10 or less | 18 | 3 | 3 | 2 | 74 | 0.4 |
| Example 14 | Na-Y type zeolite | 0.95 | 8.85 | — | 195° C. 305° C. | 10 or less | 18 | 3 | 3 | 6 | 70 | 0.4 |
| Example 15 | Na-Y type zeolite | 0.95 | 8.85 | — | 195° C. 305° C. | 10 or less | 18 | 3 | 3 | 12 | 63 | 1.5 |
| Example 16 | Na-Y type zeolite | 0.95 | 8.85 | — | 195° C. 305° C. | 10 or less | 18 | 3 | 3 | 1 | 65 | 0.2 |
| Example 17 | Na-Y type zeolite | 0.95 | 8.85 | — | 195° C. 305° C. | 10 or less | 18 | 3 | 3 | 2 | 74 | 0.4 |

| | Condition of vapor phase catalytic reaction | | | Result of vapor phase contact reaction | | | |
|---|---|---|---|---|---|---|---|
| | Space velocity of raw material gas ($h^{-1}$) | Reaction temperature (°C.) | Reaction pressure $kg/cm^2$ G | Reaction time (h) | STY of dimethyl carbonate (g/l-h) | Selectivity (%) | |
| | | | | | | Based on CO | Based on MN |
| Example 8 | 8000 | 110 | Atmospheric pressure | 0~8 50 | 280 (same level) | 84 — | 87 — |
| Example 9 | 8000 | 110 | Atmospheric pressure | 0~8 50 | 400 (same level) | 83 — | 91 — |
| Example 10 | 8000 | 110 | Atmospheric pressure | 0~8 50 | 400 (same level) | 80 — | 85 — |
| Example 11 | 8000 | 110 | Atmospheric pressure | 0~8 10 | 380 330 | 75 — | 80 — |
| Example 12 | 8000 | 110 | 3 | 0~8 50 | 480 (same level) | 83 — | 90 — |
| Example 13 | 8000 | 105 | 3 | 0~8 50 | 400 (same level) | 84 — | 88 — |
| Example 14 | 8000 | 105 | 3 | 0~8 50 | 400 (same level) | 81 — | 88 — |
| Example 15 | 8000 | 105 | 3 | 0~8 50 | 380 (same level) | 75 — | 87 — |
| Example 16 | 8000 | 105 | 3 | 0~8 50 | 380 (same level) | 80 — | 85 — |
| Example 17 | 8000 | 105 | Atmospheric pressure | 0~8 50 | 360 (same level) | 83 — | 88 — |

TABLE 3

| Characteristic of solid catalyst | | | |
|---|---|---|---|
| Carried amount of metal ion | Acid strength: | Acid amount: against | Condition of vapor phase catalytic reaction |

TABLE 3-continued

| | Kind of zeolite carrier | (% by weight) Pd++ | Na+ | Other metals | Elimination peak (°C.) | HY type zeolite (%) | Composition of raw material gas (mol %) | | | | | |
|---|---|---|---|---|---|---|---|---|---|---|---|---|
| | | | | | | | CH$_3$ONO (MN) | CO | NO | MeOH | N$_2$ | Water |
| Example 18 | Na-Y type zeolite | 0.95 | 8.86 | — | 195° C. 305° C. | 10 or less | 15 | 5 | 3 | 2 | 75 | 0.05 |
| Example 19 | Na-Y type zeolite | 1.01 | 5.58 | — | 195° C. 315° C. | 10 or less | 15 | 5 | 3 | 2 | 75 | 0.05 |
| Example 20 | Na-Y type zeolite | 0.98 | 14.3 | — | 190° C. 280° C. | 10 or less | 15 | 5 | 3 | 2 | 75 | 0.05 |
| Example 21 | Na-Y type zeolite | 2.07 | 8.43 | — | 195° C. 305° C. | 10 or less | 15 | 5 | 3 | 2 | 75 | 0.05 |
| Example 22 | Na-Y type zeolite | 1.01 | 8.44 | — | 195° C. 305° C. | 10 or less | 15 | 5 | 3 | 2 | 75 | 0.05 |
| Example 23 | Na-Y type zeolite | 1.0 | 6.40 | Ca: 4.7 | 196° C. 320° C. | 10 or less | 15 | 5 | 3 | 2 | 75 | 0.05 |
| Example 24 | Na-Y type zeolite | 1.0 | 4.80 | Li: 1.3 | 194° C. 310° C. | 10 or less | 15 | 5 | 3 | 2 | 75 | 0.05 |

| | Condition of vapor phase catalytic reaction | | | Result of vapor phase contact reaction | | | |
|---|---|---|---|---|---|---|---|
| | Space velocity of raw material gas (h$^{-1}$) | Reaction temperature (°C.) | Reaction pressure kg/cm$^2$ G | Reaction time (h) | STY of dimethyl carbonate (g/l·h) | Selectivity (%) | |
| | | | | | | Based on CO | Based on MN |
| Example 18 | 8000 | 110 | 3 | 0~8 | 380 | 88 | 81 |
| | | | | 500 | 345 | — | — |
| Example 19 | 8000 | 110 | 3 | 0~8 | 420 | 87 | 80 |
| | | | | 70 | 409 | — | — |
| Example 20 | 8000 | 110 | 3 | 0~8 | 230 | 85 | 85 |
| | | | | 70 | 210 | — | — |
| Example 21 | 8000 | 110 | 3 | 0~8 | 480 | 86 | 79 |
| | | | | 70 | 469 | — | — |
| Example 22 | 8000 | 110 | 3 | 0~8 | 355 | 86 | 81 |
| | | | | 70 | 348 | — | — |
| Example 23 | 8000 | 110 | 3 | 0~8 | 315 | 86 | 77 |
| | | | | 70 | 300 | — | — |
| Example 24 | 8000 | 110 | 3 | 0~8 | 346 | 86 | 77 |
| | | | | 70 | 340 | — | — |

EXAMPLE 25

10.1 g of NaY type zeolite (Toso K.K., HSZ-320NAA) that the atomic ratio of Si to Al is 2.75 were added to a beaker of 500 ml, and 300 ml of distilled water were added thereto, and then the mixture was boiled for one hour while stirred with a magnetic stirrer. After the filtration, 300 ml of 1N-NaNO$_3$ aqueous solution were added to the mixture and the mixture was stirred at a room temperature for 20 hours. After the obtained mixture was filtered and was washed with 200 ml of distilled water, 250 ml of distilled water were added to the mixture.

The solution obtained by dissolving 0.25 g of tetraaminepalladium chloride into 50 ml of distilled water was added dropwise to the slurry solution over 30 minutes while the slurry solution was gently stirred. After the dropwise addition, the mixture was allowed to stand for one day while stirred, and then the mixture was filtered followed by addition of 20.0 ml of distilled water. The solution obtained by dissolving 1.01 g of manganese acetate (tetrahydrate) into 100 ml of distilled water was added to the mixture over 30 minutes and the mixture was allowed to stand for one day while stirred. The catalyst containing a carried amount of 1.0% by weight of palladium and a carried amount of 1.3% by weight of manganese was prepared in the same manner as in Example 18.

When the acid strength of the above-mentioned solid catalyst was measured according to the ammonia-TPD method, desorption peaks were observed at approximately 197° C. and 330° C., and there were essentially no other peaks present at temperatures higher than the above. In addition, the acid amount of the solid catalyst (according to the ammonia-TPD method) was 10% or less (1.5 times of the catalyst in Example 18) of the acid amount of HY zeolite.

The reaction was carried out by using the obtained catalyst in the same manner as in Example 18. Dimethyl carbonate was formed at an initial space time yield (initial STY) of 410 g/l.h, the selectivity of dimethyl carbonate based on carbon monoxide was 83%, and the selectivity of dimethyl carbonate based on methyl nitrite was 75%. When the reaction continued for 70 hours, The STY was 407 g/l.h at 70 hours.

EXAMPLE 26

The catalyst containing a carried amount of 1.0% by weight of palladium and a carried amount of 2.4% by weight of cerium was prepared in the same manner as in Example 25 except for using cerium chloride (hexahydrate) instead of manganese acetate. The reaction was carried out by using the catalyst in the same manner as in Example 18. As a result, dimethyl carbonate was formed at an STY of 450 g/l.h, the selectivity of dimethyl carbonate based on carbon monoxide was 81%, and the selectivity of dimethyl carbonate based on methyl nitrite was 72%. When the reaction continued for 70 hours, the STY was 447 g/l.h at 70 hours.

When the acid strength of the above-mentioned solid catalyst was measured according to the ammonia-TPD method, desorption peaks were observed at approximately 196° C. and 345° C., and there were essentially no other peaks present at temperatures higher than the above. In addition, the acid amount of the solid catalyst (according to the ammonia-TPD method) was 15% or less (2.0 times of the catalyst in Example 18) of the acid amount of HY zeolite.

EXAMPLE 27

(Preparation of a catalyst)

In 200 ml of distilled water was dipped 10 g of Y type zeolite substituted by Na ion, and under heating to 70° C. and stirring the mixture, 50 ml of an aqueous solution containing 0.23 g (Pd: 1 mmole) of tetra-amine palladium dichloride was added dropwise over 30 minutes. After maintaining the mixture to 70° C. for 3 hours under stirring, the mixture was cooled to room temperature, filtered and washed with water. After the mixture was dipped again in 200 ml of distilled water, to the mixture was added dropwise 50 ml of an aqueous solution containing 0.68 g (Cu: 5 mmole) of cupric chloride over 30 minutes and the mixture was treated in the same manner as mentioned above. After drying the product at 100° C. for 5 hours, the product was calcinated at 300° C. for 3 hours under air-flow to prepare a catalyst in which palladium ion and copper ion were carried on Y type zeolite.

(Preparation of a diester of carbonic acid)

The above catalyst (5 ml) was filled in a vapor phase reactor (attached with an outer jacket) having an inner diameter of 20 mm, and then the reactor was fixed vertically and a heating medium was circulated in the jacket of the reactor to control a temperature in a catalyst bed to 120° C. From the upper end of the reactor, a mixed gas comprising a gas containing methyl nitrite synthesized from nitrogen monoxide, oxygen and methanol, and carbon monoxide, i.e. a mixed gas comprising a composition of 15% by volume of methyl nitrite, 10% by volume of carbon monoxide, 3% by volume of nitrogen monoxide, 6% by volume of methanol and 66% by volume of nitrogen was supplied with a space velocity (GHSV) of 4000 hr$^{-1}$ to subject the reaction under normal pressure.

Then, the reaction product passed through the reactor was captured by passing through an ice-cold methanol. The captured solution thus obtained was analyzed by gas chromatography to give the results that dimethyl carbonate was formed with STY of 250 g/l.hr, a selectivity based on carbon monoxide of 98% and a selectivity based on methyl nitrite of 79%. Also, it was confirmed that even when the reaction was carried out for 50 hours continuously, both of STY and selectivities were not changed at all.

EXAMPLE 28

(Preparation of a catalyst)

In the same manner as in Example 1 except for using 0.97 g of ferric chloride in place of 0.68 g of cupric chloride, a catalyst in which palladium ion and ferric ion were carried on Y type zeolite was prepared.

(Preparation of a diester of carbonic acid)

By using the above catalyst, reaction was carried out in the same manner as in Example 1. The reaction product passed through the reactor was captured by passing through an ice-cold methanol. The captured solution thus obtained was analyzed by gas chromatography to give the results that dimethyl carbonate was formed with STY of 230 g/l.hr, a selectivity based on carbon monoxide of 97% and a selectivity based on methyl nitrite of 78%. Also, it was confirmed that dimethyl oxalate, carbon dioxide and methyl formate were formed as by-products. It was also found that even when the reaction was carried out for 50 hours continuously, catalyst activity was substantially not changed.

EXAMPLE 29

(Preparation of a catalyst)

In the same manner as in Example 1 except for using 10 g of X type zeolite in place of 10 g of Y type zeolite, a catalyst in which palladium ion and copper ion were carried on X type zeolite was prepared.

(Preparation of a diester of carbonic acid)

By using the above catalyst, reaction was carried out in the same manner as in Example 1. The reaction product passed through the reactor was captured by passing through an ice-cold methanol. The captured solution thus obtained was analyzed by gas chromatography to give the results that dimethyl carbonate was formed with STY of 180 g/l.hr, a selectivity based on carbon monoxide of 95% and a selectivity based on methyl nitrite of 80%. Also, it was confirmed that dimethyl oxalate, carbon dioxide and methyl formate were formed as by-products. It was also found that even when the reaction was carried out for 50 hours continuously, catalyst activity was substantially not changed.

EXAMPLE 30

(Preparation of a catalyst)

In the same manner as in Example 1 except for using 0.49 g (Ce: 2 mmole) of cerium chloride in place of cupric chloride, a catalyst in which palladium ion and cerium ion were carried on Y type zeolite was prepared.

(Preparation of a diester of carbonic acid)

By using the above catalyst, reaction was carried out in the same manner as in Example 1. As the results, it was found that dimethyl carbonate was formed with STY of 400 g/l.hr, a selectivity based on carbon monoxide of 77% and a selectivity based on methyl nitrite of 79%. It was also understood that even when the reaction was carried out for 50 hours continuously, catalyst activity was substantially not changed.

EXAMPLE 31

(Preparation of a catalyst)

In the same manner as in Example 1 except for using 0.34 g of (2 mmole) silver nitrate in place of cupric chloride, a catalyst in which palladium ion and silver ion were carried on Y type zeolite was prepared.

(Preparation of a diester of carbonic acid)

By using the above catalyst, reaction was carried out in the same manner as in Example 1b-7b. As the results, it was found that dimethylcarbonate was formed with STY of 380 g/l.hr, a selectivity based on carbon monoxide of 78% and a selectivity based on methyl nitrite of 78%. It was also found that even when the reaction was carried out for 50 hours continuously, catalyst activity was substantially not changed.

EXAMPLE 32

(Preparation of a catalyst)

In the same manner as in Example 1 except for using 0.35 g of (2 mole) manganese acetate in place of cupric chloride, a catalyst in which palladium ion and manganese ion were carried on Y type zeolite was prepared.

(Preparation of a diester of carbonic acid)

By using the above catalyst, reaction was carried out in the same manner as in Example 1. As the results, it was found that dimethyl carbonate was formed with STY of 410 g/l.hr, a selectivity based on carbon monoxide of 81% and a selectivity based on methyl nitrite of 81%. It was also found that even when the reaction was carried out for 50 hours continuously, catalyst activity was substantially not changed.

COMPARATIVE EXAMPLE 1

(Preparation of a catalyst)

In 100 ml of 5N hydrochloric acid were dissolved 0.35 g of palladium chloride and 0.34 g of cuptic chloride (dihydrate), and after dipping 10 g of granular activated charcoal therein, the mixture was filtered and the filtrate was washed with water and dried at 100° C. to prepare a catalyst ($PdCl_2$—$CuCl_2$/C) carried palladium chloride and cupric chloride on the activated charcoal.

(Preparation of a diester of carbonic acid)

By filling 5 ml of the above catalyst in place of the catalyst of Example 1, reaction was carried out in the same manner as in Example 1. The reaction product passed through the reactor was captured by passing through an ice-cold methanol. The captured solution thus obtained was analyzed by gas chromatography to give the results that dimethyl carbonate was formed with STY of 280 g/l.hr, a selectivity based on carbon monoxide of 96% and a selectivity based on methyl nitrite of 93%. However, continuing the reaction, STY and selectivities were gradually lowered and after 50 hours from initiation of the reaction, STY, a selectivity based on carbon monoxide and a selectivity based on methyl nitrite became 150 g/l.hr, 85% and 89% respectively.

The vapor phase reaction of carbon monoxide and a nitrite can be carried out under gentle conditions by using a catalyst in which alkali metal ion, alkaline earth metal ion, hydrogen ion or ammonium ion of zeolite is replaced by a platinum group metal ion and a second component metal ion selected from copper, iron, tin, nickel, cobalt, cerium, silver and manganese, whereby a diester of carbonic acid can be obtained with high selectivity and high yield. Also, since the catalyst of the present invention contains no chlorine component, it does not corrode a reaction apparatus and lifetime of the catalyst can be elongated with a great extent.

The process of the present invention allows the preparing of carbonic diester (dimethyl carbonate) to be carried out for a long period of time at both high selectivity and high yield by carrying out a vapor phase catalytic reaction of carbon monoxide and alkyl nitrite (e.g., methyl nitrite) in the presence of a solid catalyst wherein platinum group metal ion is exchanged on an ion exchange carrier such as zeolite.

We claim:

1. A process for preparing carbonic diester comprising the formation of carbonic diester by the vapor phase catalytic reaction of an alkyl nitrite and carbon monoxide in the presence of a solid catalyst, wherein platinum group metal ion in the solid catalyst is exchanged on an ion exchange zeolite carrier.

2. The process according to claim 1, wherein the molar ratio of said nitrite to carbon monoxide is 2:1 or more.

3. The process according to claim 1, wherein said catalyst comprises the platinum group metal ion and at least one ion of a metal selected from the group consisting of copper, iron, tin, nickel, cobalt, cerium, silver and manganese carried on said zeolite.

4. The process according to claim 1, wherein said catalyst comprises the platinum group metal ion and at least one ion of a metal selected from the group consisting of an alkaline metal and an alkaline earth metal exchanged on an ion exchange zeolite.

5. The process according to claim 1, wherein the atomic ratio of Si to Al of said zeolite is 0.5 to 10.

6. The process according to claim 1, wherein said reaction is carried out in the presence of 0.01 to 5 mol % of water against the total amount of a raw material gas supplied to the reaction system.

7. The process according to claim 1, , wherein the molar ratio of said nitrite to carbon monoxide is 2:1 to 30:1.

8. The process according to claim 7, wherein the molar ratio of said nitrite to carbon monoxide is 2:1 to 20:1.

9. The process according to claim 8, wherein the molar ratio of said nitrite to carbon monoxide is 3:1 to 10:1.

10. The process according to claim 6, wherein the ratio of water is 0.1 to 3 mol %.

11. The process according to claim 4, wherein said reaction is carried out in the presence of 0.01 to 5 mol % of water and 0.03 to 30 mol % of a lower aliphatic alcohol against the total amount of the raw material gas supplied to the reaction system.

12. The process according to claim 1, wherein a space velocity of the raw material gas containing carbon monoxide and a nitrite to be reacted is in the range of 500 to 20000 $h^{-1}$.

13. The process according to claim 1, wherein said reaction is carried out at 0° to 200° C. under an atmospheric pressure.

14. The process according to claim 1, wherein a carried amount of a platinum group metal ion is 0.1 to 10% by weight based on the zeolite carrier.

15. The process according to claim 3, wherein a carried amount of at least one ion of a metal is 1 to 50 gram atomic equivalent based on the amount of the platinum group metal ion.

16. The process according to claim 1, wherein said ion exchange type zeolite is at least one selected from the group consisting of a synthetic zeolite such as X type zeolite, Y type zeolite, mordenite and silicalite and a natural zeolite.

17. The process according to claim 1, wherein said catalyst has weak acidity shown by an acidic strength or an acidic amount.

18. The process according to claim 1, wherein the acidic strength of the catalyst is a desorption temperature below 360° C. according to an ammonia-TPD method.

19. The process according to claim 1, wherein the acidic amount determined by an ammonia-TPD method is 20 or less in the case where an acidic amount of an HY type zeolite is 100.

* * * * *